(12) United States Patent
Lillard et al.

(10) Patent No.: US 8,568,784 B2
(45) Date of Patent: Oct. 29, 2013

(54) NANOPARTICLES FOR DELIVERY OF ACTIVE AGENTS

(75) Inventors: James W. Lillard, Smyrna, GA (US);
Rajesh Singh, Atlanta, GA (US);
Shailesh Singh, Atlanta, GA (US)

(73) Assignee: Morehouse School of Medicine, Atlanta, GA (US)

( * ) Notice: Subject to any disclaimer, the term of this patent is extended or adjusted under 35 U.S.C. 154(b) by 444 days.

(21) Appl. No.: 12/943,588

(22) Filed: Nov. 10, 2010

(65) Prior Publication Data

US 2011/0052710 A1 Mar. 3, 2011

Related U.S. Application Data

(63) Continuation of application No. 11/725,562, filed on Mar. 20, 2007, now Pat. No. 8,231,907.

(60) Provisional application No. 60/783,858, filed on Mar. 21, 2006.

(51) Int. Cl.
*A61K 9/14* (2006.01)

(52) U.S. Cl.
USPC ........... 424/493; 424/491; 424/492; 424/497; 424/494; 424/490; 424/489

(58) Field of Classification Search
USPC .................. 424/489, 490, 491, 492, 493, 494
See application file for complete search history.

(56) References Cited

U.S. PATENT DOCUMENTS

| | | | |
|---|---|---|---|
| 6,126,097 A | 10/2000 | Chen et al. | |
| 2003/0203205 A1* | 10/2003 | Bi et al. | 428/402 |
| 2007/0190160 A1* | 8/2007 | Turos et al. | 424/490 |

FOREIGN PATENT DOCUMENTS

| | | |
|---|---|---|
| CA | 2353809 | 6/2000 |
| EP | 0600528 | 6/1994 |
| EP | 0958813 | 11/1999 |
| EP | 1270006 | 1/2003 |
| WO | 96/20698 | 7/1996 |
| WO | 99/61002 | 12/1999 |
| WO | 01/41762 | 6/2001 |
| WO | 01/47501 | 7/2001 |
| WO | 01/78786 | 10/2001 |
| WO | 2004064752 | 8/2004 |
| WO | 2004/091571 | 10/2004 |
| WO | 2007/070843 | 6/2007 |

OTHER PUBLICATIONS

Park et al. (Preparation and characterization of methoxy poly(ethylene glycol)/poly($\epsilon$-caprolactone) amphiphilic block copolymeric nanospheres for tumor-specific folate-mediated targeting of anticancer cells, Biomaterials 26, 2005, pp. 1053-1061).*
Communication and Supplementary European Search Report, Application No. 07753470.9-2112/2012751 PCT/US2007006844, dated Oct. 22, 2010.
International Search Report, International Preliminary Report on Patentability and the Written Opinion of the International Seacrh Authority for PCT/US2007/006844, Oct. 22, 2010.
Mueler-Eckhardt et al., "High-dose IgG treatment for neonatal alloimmune thrombocytopenia", Annals of Hematology, vol. 59, No. 1, 1989, pp. 145-146.

* cited by examiner

*Primary Examiner* — Rebecca Prouty
*Assistant Examiner* — Danielle Sullivan
(74) *Attorney, Agent, or Firm* — Ping Wang; Andrews Kurth LLP

(57) ABSTRACT

Milled nanoparticles comprising a biologically active agent, at least one biopolymer and a coating containing at least one coating which is a polymer or ligand are produced using milling and coating techniques which have not previously been used for these applications.

20 Claims, No Drawings

NANOPARTICLES FOR DELIVERY OF ACTIVE AGENTS

This application is a continuation application of U.S. patent application Ser. No. 11/725,562, filed on Mar. 20, 2007 now U.S. Pat. No. 8,231,907, issued on Jul. 31, 2012, which claim the priority of Provisional Patent Application Ser. No. 60/783,858, filed on Mar. 21, 2006. The entirety of the aforementioned applications is incorporated herein by reference.

FIELD

This invention relates to the preparation and use of coated nanoparticles wherein nanoparticles containing the bioactive agent in an excipient is coated with a ligand or polymer, preferably, with a lactone and/or glycol. Exemplified are such nanoparticles coated with at least one coating agent chosen from among of polycaprolactone (PCL) and polyethylene glycol (PEG). The nanoparticles of the invention are produced using milling and coating techniques which have not previously been used to make particles containing bioactive agents and are made using polymer-coating and milling techniques, for use as carrier systems for the mucosal or systemic delivery of biologicals.

BACKGROUND

Most widely used vaccines are presently administered by systemic routes. In many cases these vaccines are effective in inducing systemic cell-mediated and systemic antibody responses, but are poor at inducing mucosal immunity in humans who have not had a previous mucosal infection by the causative organism. Many therapeutic biologicals (e.g., insulin, anti-tumor necrosis factor-alpha antibody, interferon-alpha, erythropoietin) are, like vaccines, delivered parenterally to avoid degradation by gastrointestinal secretions. A number of strategies are available to increase the efficacy of mucosally administered molecules. Common approaches involve the avoidance or modification of gastrointestinal secretions by the use of gastric inhibitors, protease and acid resistant films or encapsulation. Substrates used for oral delivery of these agents, which may have adjuvant activity, may include liposomes. The incorporation of molecules in liposomes or polymers can protect them from harmful digestive secretions.

The development of controlled release biologically-compatible systems using polymers has provided means for obtaining sustained release of biologically active agents. Recently, biodegradable polymeric microspheres have received much attention for the purpose of controlled release of antigens to eliminate the need for refrigeration, to reduce the number of immunization and to control dosage.

U.S. Pat. No. 4,744,933 also discloses the process of encapsulating bioactive materials. For example, the adjuvant effect of microspheres made of poly-DL-lactide-co-glycolide (DL-PLG) copolymer containing Staphylococcal enterotoxin B (SEB), when subcutaneously (sc) injected in to mice, was comparable to that of Freund's complete adjuvant (FCA). Ovalbumin (OVA) a poor immunogen when entrapped in DL PLG microparticles induced significantly higher levels of IgG antibodies in mice following primary immunization than did OVA in FCA.

U.S. Pat. No. 5,453,368 discloses a method for encapsulating a biological substance in biocompatible microcapsules. Additionally, it discloses the coating of the microcapsules with solution of a soluble organic polymer in an organic solvent.

U.S. Pat. No. 5,879,713 teaches the targeted delivery of small molecules such as nucleic acids and peptides. Delivery systems such as emulsions, liposomes and microspheres are widely regarded as protein carriers. As with other peptide and macro-molecular therapeutics or biologicals, the rate of release of antigens from biodegradable microspheres was shown to be dependent mainly on degradation of the polymeric matrix. Particulate delivery systems such as microspheres can also possess adjuvant activity when used as oral vehicles for antigens. Unfortunately, the current methods for generating microspheres, often made of lipids or polymers, require oil-water emulsion techniques that waste antigen or therapeutic protein and may alter the conformation of the encapsulated active agents, an important consideration in administration of polypeptides.

SUMMARY

This invention provides a novel and relatively inexpensive preparation technique for the generation of nanoparticles through planetary ball milling, which allows for controlling the size of the particle (5 nm to 60 μm mean size) with >99% loading efficiency, polymer or ligand coating for controlled, protected and targeted release and delivery of their contents. The nanoparticles produced thereby contain the desired biologically active agent(s) or fluorescent, bioluminescent, and/ or radio-isotope agents in a biopolymer excipient such as alginate, cellulose, starch or collagen. The coating of the nanoparticles as exemplified herein contains polycaprolactone or polyethylene glycol or both.

DETAILED DESCRIPTION

Controlled released nano- or micro-particles can either enhance immunity by providing a long-term suppository or "depot" for antigen or can deliver complex molecules for mucosal or parental delivery. Often the size of these particles contributes to their effectiveness. Nano- and micro-particle uptake from the gastrointestinal track often involves the villus tips, enterocytes, and Peyer's patches. The factors controlling the extent of this uptake include, but are not limited to, size, hydrophobicity, surface charge, dose, and timing of food intake. Particles ranging 5 to 150 μm enter via the villus tips, while enterocytes and other host cells take up particles<100 ηm in size. Peyer's patches are the predominant site of uptake for particles<10 μm, with particles<5 μm being transported into the lymph. Relatively positively surface-charged (>−0.1 mV) particles are more efficiently taken up by M cells that predominate the Peyer's patch. Hence, positively charged particles<1 μm and >−0.1 mV may be favored for oral delivery of vaccines since they would presumably have a higher propensity to penetrate the mucosa. Similarly, nanoparticles (<200 nm) may be preferentially taken up by host cells (i.e., leukocytes, epithelial cells, cancer cells, etc.).

It is the purpose of this invention to provide novel methods for the preparation and modification of biodegradable and biocompatible nano- and micro-particles. These particles were characterized by size, surface charge and morphology. Polycaprolactone-coated, biopolymer (e.g., alginate, cellulose, and/or starch)-polyethylene glycol matrix (PCL-XP) particles were prepared by milling techniques that produce recombinant protein, therapeutic (e.g., cisplatin, paclitaxel, etc.) or diagnostic (e.g., infrared fluorophore (e.g., indocyanine green), radioisotope (e.g., technetium-99 m), 18F-5-fluorodeoxyuridine, gadolinium, ferric oxide, cobalt, boron, rhenium, etc) molecule-containing particles of a controlled size (selectable range: 0.005 to 60 μm mean size). The studies relating to percent entrapment and loading studies with bovine serum albumin (BSA), immunoglobulin G (IgG), Texas Red (TR), cisplatin, and gadolinium showed ~100% entrapment efficiency and ~20% of loading per weight of the particles could be achieved. Anti-cancer agent can, for example, include such agents as, carboplatin, vinca-alkaloids, bleomycin, podophylotoxins, methotrexate, cytarabine, fluorouracil, mercaptopurine, thioguanine, hydroxyurea, procarbazine, asparaginase, nitrosoureas, dactinomycin, mitomycin, dacarbazine, doxorubicin, daunomycin, cyclophosphamide, chlorambucil, busulfan, mechlorethamine, melphalar, lithium/magnesium/aluminum/titanium/manganese/copper/zinc/gallium/gold/metallotherapeutics, 2-carboxyethylgermanium sesquioxide, spirogermanium, germatrane, budotitane, titanocene dichloride, vanadium, organosilicon compounds, arsenic, selenium, technetium, ruthenium, rhodium, palladium and bismuth. The ability to target particular cell types with an anti-cancer agent as exemplified below in the case of prostate cancer cells as exemplified herein, makes the instant invention of particular value.

Other biologically active compounds which could beneficially be used in the method of the invention include chemopreventive agents such as *Withania somnifera, Curcuma longa, Melia azadirachta, Terminalia Arjuna, Tinospora cordifolia, Tribulus Terrestris, Zingiber officinale, Capsicum annum*, capsaicinoids, and steroidal saponins. Proteins which could be advantageously administered by the methods of the invention include, but are not limited to, therapeutic proteins and peptides including hormones, cytokines, monoclonal antibodies, enzymes. Macromolecules such peptides that selectively bind major histocompatibility complexes and T cell receptors could also be advantageously administered using methods of the invention.

Targeting proteins or peptides that would be particularly of value include those that selectively bind dentritic cells, B cells, macrophages, cancer cells, edothelial cells and B cell recptors.

Generally, there are two types of mills that have been employed for making particles: vibratory or planetary ball mills. The vibratory ball milling grinds powders by high velocity impact while planetary ball mill uses more of a grinding motion. Typically, planetary ball milling has only been used to generate micron-sized particles, while vibratory milling can yield nano-particles. However, the high impact resulting from the vibratory milling technique makes incorporating biologicals difficult. Planetary ball mills pulverize and mix materials ranging from soft and medium to extremely hard, brittle and fibrous materials. Both wet and dry grinding can be carried out. Minerals, ores, alloys, chemicals, glass, ceramics, plant materials, soil samples, sewage sludge, household and industrial waste and many other substances can be reduced in size simply, quickly and without loss. Planetary ball mills have been successfully used in many industrial and research sectors, particularly wherever there is high demand for purity, speed, fineness and reproducibility. The planetary ball mills produce extremely high centrifugal forces with very high pulverization energies and short grinding times. Because of the extreme forces exerted in the use of vibratory and planetary ball mills the formulation of therapeutics has not been practiced previously as described herein.

The method of this invention results in particle generation and encapsulation of biologicals and pharmaceuticals enabling precise excipient/biopolymer and PEG concentrations, curing conditions, and planetary ball milling to generate either nano- and micro-particles of a controllable size without altering the encapsulated contents. The formulation of PCL-XP particles allows for the programmed time- and/or targeted-release of entrapped molecules. Using the method of the invention, particles are produced wherein the core nano-matrix consists of biopolymer(s) (e.g., alginate, cellulose, collagen, lactose and/or starch) plus PEG or PCL. The particles are coated by PCL, PEG and/or modified (e.g., lysine, peptide, folic acid) to control the time and target of release of contents. The increased mechanical strength, stabilization and targeted delivery or binding of the particles is also an important aspect of the invention. (Prior art polymer-based microspheres are often beads or hydrogels that are not as efficient in protein-loading or targeting due to their size and the inability to modify their coating.) Using the methods of the invention, the PCL-XP particles, macro- (e.g., apolipoprotein E, antibody, tetanus toxoid, etc.) as well as small- (e.g., paclitaxel, cisplatin, gadolinium, etc.) molecules can be entrapped in the polymer-PEG matrix, which can subsequently be coated with PCL for extended release. The PCL may be modified for cell targeting. Hence, the resulting PCL-XP particles can deliver soluble or insoluble biologicals, heavy metals and/or therapeutics across mucosal surfaces or can solubulize previously insoluble molecules for parenteral administration. Further, modification (e.g., peptides, folic acid, antibodies, etc.) of PCL can enable targeted delivery of therapeutic or cytotoxins to tissue or organs (e.g., tumor cells) that are poorly tolerated by the host otherwise.

The method of this invention results in particle generation and encapsulation of biologicals and pharmaceuticals enabling precise excipient/biopolymer and PEG concentrations, curing conditions, and planetary ball milling to generate either nano- and micro-particles of a controllable size without altering the encapsulated contents. The formulation of PCL-XP particles allows for the programmed time- and/or targeted-release of entrapped molecules. Using the method of the invention there are produced particles wherein the core nano-matrix consists of biopolymer(s) (e.g., alginate, cellulose, collagen, lactose, etc.) plus PEG, which are coated by PCL or modified (e.g., lysine, peptide, folic acid, etc.) to control the time of release of contents. The increased mechanical strength, stabilization and targeted delivery or binding of the particles is also an important aspect of the invention. (Prior art polymer-based microspheres are often beads or hydrogels that are not as efficient in protein-loading or targeting due to their size and inability to modify their coating.) Using the methods of the invention, the PCL-XP particles, macro- (e.g., apolipoprotein E, antibody, tetanus toxoid, etc.) and small- (e.g., paclitaxel, cisplatin, gadolinium, etc.) molecules can be entrapped in the polymer-PEG matrix, which can be subsequently coated with PCL for extended release or PCL modified for cell targeting. Hence, the resulting particles can deliver soluble or insoluble biologicals, heavy metals, diagnostic agents and/or therapeutics across mucosal surfaces or solubulize previously insoluble molecules for parenteral administration.

Materials and Methods

Preparation of Particles

First, 10 to 15% (w/v) of alginate, cellulose or starch (excipient/biopolymer) was dissolved in $dH_2O$ and mixed using a homogenizer. Next, 10 to 20% protein (e.g., BSA or IgG) or macromolecule (e.g., gadolinium, paclitaxel, or cisplatin) (w/v) at 4° C. was added to the excipient/biopolymer solution. Next, 10% of PEG (w/v) was added to the biopolymer-protein or—macromolecule solution and stirred for 30 minutes. After centrifugation, the solution was poured into ~3 $mm^3$ tablets and dried. These tablets were then milled using planetary ball milling under controlled temperature (<37° C.). The resulting particles were either used alone (i.e., uncoated) or coated with a 5%, 10% or 20% PCL solution (in methylene chloride) by continuous stirring at 1000 rpm. The PCL-coated bio-polymer-PEG particles were finally rinsed with $dH_2O$, dried and stored as a powder.

PCL Activation and Peptide Conjugation

PCL was activated to attach peptide or substrates (i.e., folic acid) to its surface for targeted delivery of particles. First, 2 g of PCL was dissolved in 6 ml of dry dioxane and heated in a 50° C. water bath for 2 hours to solubilize the polymer and then cooled at room temperature (RT). A 2 ml solution of N,N' disuccinimidylcarbonate (153.7 mg/ml in dry acetone) and 2 ml of a pyridine solution (4.745 mg/ml in dry acetone) was mixed with the PCL suspension with continuous stirring for 6 hours at RT. The mixture was next filtered using a G2 glass fiber with 1 .mu.m pore size to remove precipitates. The resulting supernatant was precipitated with 4 volume of diethyl ether. The precipitant was resuspended in acetone and precipitated again with diethyl ether. The activated or reactive PCL was then dried and stored at 4° C.

The activated PCL was then conjugated to lysine(s) or any free amine group from a peptide. The desired peptide or amino acid (e.g., lysine) was dissolved in 0.1 M $Na_2HPO_4$, 0.1 M boric acid, pH 8.5 at a concentration of 2 mg/ml. Next, the activated PCL, dissolved in acetonitrile, was mixed with stirring to the peptide or amino acid at a ratio of 8:1 (activated PCL:peptide or amino acid) overnight at 4° C. The excess activated and unconjugated PCL was removed by filtration using a glass filter.

Coating of Particles

Particles of known quantity and size were coated with various concentrations (e.g. 5%, 10% and 10%) of PCL or amine-conjugated PCL dissolved in methylene chloride with continuous stirring (1000 rpm). The resulting PCL-coated particles were separated from the PCL coating solution by draining the supernatant after centrifugation. The resulting PCL coated nanospheres were strained, air-dried and stored at 4° C.

Thermal Analysis

Differential scanning calorimetry (DSC) was carried out using a PerkinElmer Diamond DSC and thermogravimetric/differential thermal analysis. First, ~1 mg of particles were heated from 30° C. to 250° C. at a constant rate (10° C. per minute), in atmospheric nitrogen. A thermal gravimetric profile of the particles was then performed.

Quantification and Characterization of Protein Loading

In vitro release studies of PCL-coated bio-polymer-PEG particles after incorporation of their contents were carried out in phosphate buffered saline pH 7.4 at 37° C. Approximately, 100 mg of particles were suspended and digested in a 100 ml of PBS or citrated tris buffer at 37° C. to determine their rate of release. Particles were also filtered using 0.1, 0.22, or 0.45 µm Millipore filter(s). Protein-containing contents were dissolved in either PBS or citrated tris buffer saline and the rate of release was measured using the Lowry's protein assay. In the case of polymer-coated particles, samples were collected every 48 hours, while replacing the PBS to mimic the infinite sink conditions of the host.

Circular dichrosim spectrum analysis was also used to assess the regularity of molecular assemblies comparing standard or encapsulated protein (e.g., BSA or IgG). The conformations of the intra-molecular structures (e.g., alpha helical, beta sheets, etc.) of the released protein were determined by measuring their circular dichroism, in terms of $\Delta\epsilon$, and comparing them to unencapsulated protein as standards.

Particle Size, Charge and Morphology Analysis

Particles were analyzed for their particle size by laser diffraction using Malvern particle size and charge analyzer (Zetasizer). Particles were dispersed in $dH_2O$ and analyzed for charge and size. The surface morphology of the PCL-coated bio-polymer-PEG particles was characterized by scanning electron microscopy (SEM). For SEM analysis, particles were prepared by dispensing the dried particles onto one side of a double adhesive tape, which was stuck to an aluminum stub. The stubs were then coated with gold using Polaron SC S00-sputter coater, to a thickness of 20 to 30 nm. The samples were then introduced into the specimen chamber of a scanning electron microscope and examined for surface morphology. The infrared spectra of the different stages of the PCL-coated bio-polymer-PEG particle formulations were obtained by first mixing 1 mg of the samples with 100 mg of dried potassium bromide powder. Next, infrared spectra of the samples were assayed using a Fourier transformed infra red spectrometer.

For sizing the nanoparticles, the following directions provide a guide. In general, particle size ranging from 5 to 30 nm, 30 to 180 nm, 0.2 to 1 µm, 1 to 6 µm, 4 to 12 µm or 10 to 60 µm can be controlled by using a 50 ml grinding jar filled with one to three 20 mm and ten to sixteen 10 mm balls along with the sample to be encapsulated and the excipient using grinding speed maintained at 200 to 400 rpm. This grind interval should be set for 10 minutes followed by a resting cycle for 15 minutes. Ten to twenty-five cycles (grind and rest) allow for >99.5% particles of size ranging from 5 to 30 nm, 30 to 180 nm, 0.2 to 1 µm, 1 to 6 µm, 4 to 12 µm or 10 to 60 µm. When the size of the grinding jar is increased to >50 ml (e.g., 125 ml, 500 ml, etc.), the number of balls are increased proportional to the increase in jar volume.

Examples of Particle Size Modulation by Grinding Ball and Active-Resting Cycles

The particle size ranging from 5 to 30 nm can be obtained using a 50 ml grinding jar filled with three 20 mm and ten 10 mm balls along with the sample to be encapsulated and excipient, using grinding speed maintained at 400 rpm. This grind interval is set for 10 minutes followed by a resting cycle for 15 minutes. Fifteen to twenty-five cycles (grind and rest) result in >99.5% particles of size ranging from 5 nm to 30 nm.

Particle size ranging from 30 to 180 nm can be obtained using a 50 ml grinding jar filled with three 20 mm and ten 10 mm balls along with the sample to be encapsulated and the excipient, using the grinding speed maintained at 400 rpm. This grind interval should be set for 10 minutes followed by a resting cycle for 15 minutes. Fifteen to twenty cycles (grind and rest) result in >99.5% particles of size ranging from 30 to 180 nm.

Particle size ranging from 0.2 to 1 µm can be obtained by using 50 ml grinding jar filled with three 20 mm and ten 10 mm balls along with the sample to be encapsulated and excipient, using grinding speed maintained at 300 rpm. This grind interval should be set for 10 minutes followed by a resting cycle for 15 minutes. Fifteen to twenty cycles (grind and rest) result in >99.5% particles of size ranging from 0.2 to 1 µm.

Particle size ranging from 1 to 6 µm can be obtained by using 50 ml grinding jar filled with two 20 mm and thirteen 10 mm balls along with the sample to be encapsulated and excipient, using grinding speed maintained at 300 rpm. This grind interval should be set for 10 minutes followed by a resting cycle for 15 minutes. Twenty to twenty-five cycles (grind and rest) result in >99.5% particles of size ranging from 1 to 6 µm.

Particle size ranging from 4 to 12 μm can be obtained using 50 ml grinding jar filled with two 20 mm and thirteen 10 mm balls along with the sample to be encapsulated and excipient, using grinding speed maintained at 250 rpm. This grind interval should be set for 10 minutes followed by a resting cycle for 15 minutes. Fifteen to twenty cycles (grind and rest) result in >99.5% particles of size ranging from 4 to 12 μm.

Particle size ranging from 10 to 60 μm can be obtained by using 50 ml grinding jar filled with one 20 mm and sixteen 10 mm balls along with the sample to be encapsulated and excipient, using grinding speed maintained at 200 rpm. This grind interval should be set for 10 minutes followed by a resting cycle for 15 minutes. Ten to fifteen cycles (grind and rest) allow for >99.5% particles of size ranging from 10 to 60 μm.

Effect of Excipient/Biopolymer Concentration on Particle Characteristics

Particles with diverse size (5 nm to 60 μm±10% of mean size) were produced using ~10% (w/v) of sodium alginate, ~8% (w/v) of cellulose or ~10% (w/v) of starch in $dH_2O$ (excipient/biopolymer solutions). Below 2% (w/v) of sodium alginate, cellulose or starch, the yield of particles with a mean size that did not vary >10% was found to be low. At greater than 15% of the sodium alginate or 10% of cellulose, the excipient/biopolymer solutions remained highly viscous and could not be used for tablet formation and subsequent particle preparation. Similarly, the starch (excipient/biopolymer) solution required heating to 50° C. for 20 minutes for optimal solubility and viscosity and the concentration of starch could not exceed 12% (w/v). The viscosity of the excipient/biopolymer solutions also had a significant influence on the morphology of the particles. Particles became smoother and spherical with increasing concentrations of excipient/biopolymer solution (>1% (w/v)). However, <10% excipient/biopolymer solution produced the ideal size of particle. Optimum yield was achieved with the concentrations at 10%, 8%, or 10% (w/v) of sodium alginate, cellulose or starch, respectively, for the generation of nano- or micro-particles. Hence, in subsequent studies, these optimal concentrations were prepared for the generation of 3 $mm^3$ tablets for milling into particles.

Effect of Milling Speed and Size of Planetary Balls on Particle Size

The grinding speed of the planetary ball milling apparatus (Retsch PM100) and the size of the milling balls played a significant role in controlling the particle size, as indicated in the examples above. Varying the speed from 0 to 100 rpm for 20 minutes and using ten 10 mm plus three 20 mm balls, resulted in particles ranging 20 to 50 μm in size, while speeds 100 to 200 rpm for 20 minutes yielded 10 to 20 μm microparticles. Modulating speeds from 200 to 300 rpm for 20 minutes and using fifty 5 mm plus fifteen 10 mm balls resulted in particles 1 to 5 μm in size. Increasing speeds from 300 to 400 rpm and using one hundred 5 mm ball resulted in particles ranging 0.5 to 1 μm.

To generate particles<500 nm, tablets were first milled to produce microparticles—20 to 50 μm in size. The resulting microparticles were further milled at 400 to 600 rpm for 20 minutes using one hundred 3 mm plus five hundred 2 mm balls to produce nanoparticles ranging from 5 to 500 nm in size. Further increases in speed did not have any significant effect on size reduction.

Particle Protein Entrapment and Loading Efficiencies

BSA loading could be varied from 4 to 25% (w/v). The resulting particles formed after milling became aggregated and morphologically malformed at >20% (w/v) loading of protein. A maximum of ~20% BSA loading in the nano- or micro-particles could be achieved with 100% efficiency.

Morphologies of Uncoated and PCL-Coated Bio-Polymer-PEG Particles

It is evident from SEM that the particles modified by PCL-coating appeared smooth and uniform compared to the uncoated particles. Additional smoothing of particle surface characteristics occurred with multiple PCL coatings. However, the surface of the particles changed from smooth and spherical to rough, non-spherical and vacuolated after in vitro content release.

Infrared Spectra of Uncoated and Coated Particles

The infrared spectral analysis of particles was used to denote the potential cross-linking of excipient/biopolymer(s) with proteins as well as the differences between PCL-coated and uncoated particles. Infrared spectrum of sodium alginate shows an absorption band at 3,310 $cm^{-1}$, which corresponds to the stretching frequency of —OH. Absorption in the region of 1,614 $cm^{-1}$, corresponds to the C=O bond and carboxylate (COO) group of alginate. The infrared spectrum of alginate particles loaded with BSA showed the characteristic amide absorption band at 1,660 $cm^{-1}$, which was due to the incorporated BSA in the particles. The infrared spectra of PCL also showed characteristic lactone band at 1740 $cm^{-1}$. The infrared absorbance profile of the PCL-XP (alginate) particles loaded with BSA displayed absorption bands for BSA (1,550 $cm^{-1}$), alginate (1,614 $cm^{-1}$) and PCL (1,740 $cm^{-1}$). Taken together, the infrared spectra of the particles showed that BSA was effectively incorporated in the particles without cross-linking.

Thermal Analysis of Uncoated and PCL-Coated Particles

Thermal analysis was carried out to further determine cross-linking and the stability of the particles, along with the encapsulated contents. The endothermic peak of alginate occurred at 109° C., due to dehydration compared to the same particles loaded. BSA in coated or uncoated PCL gave an endothermic peak at 118° C. The particles coated with PCL had greater stability and dehydration peak that appeared at 127° C. In the case of PCL-coated particles (PCL-coated bio-polymer-PEG), a sharp endothermic peak appeared at 360° C. due to the phase transition of PCL. The thermo gravimetric analysis of sodium alginate, alginate particles, alginate particles loaded with BSA and coated with PCL showed a first stage −20% weight loss, due to the elimination of water molecules. The complete decomposition of PCL-coated particles revealed a peak that appeared at 370° C., which indicate the increased stability of the PCL-coated particles compared to uncoated particles.

Conformational Integrity of Entrapped BSA

The standard or uncapsulated BSA and the BSA released from the PCL-coated bio-polymer-PEG particles were virtually identical. Circular dichroism analysis revealed that the helical peak and alpha helical structures of BSA remained intact when compared to control BSA, which is different from currently available alginate microspheres that alter protein conformations when formulated. This clearly indicates that the protein did not interact chemically with the matrix material or altered by the planetary milling process. These results demonstrated that the method adopted for the encapsulation of BSA into PCL-coated bio-polymer-PEG particles did not lead to a significant or irreversible aggregation or degradation of the carrier molecule.

Zeta Potential Measurements

The single-coated PCL-coated bio-polymer-PEG particles displayed greater negative charges (−55.2±0.3 mV), in comparison with latex or polylactide nanospheres (−50.9 to 46.0 0.4). PCL-coated bio-polymer-PEG particles, loaded with BSA, displayed surface charges of −6.6±0.3 mV. This may be due to the net positive charge of BSA. Additional PCL-coatings further reduced the surface charge. The surface charge could also be modulated by conjugating lysine (mono-lysine, di-lysine, tri-lysine, and tetra-lysine) to PCL before coating of particles using PCL chemically modified PCL or using PCL plus PEG for coating.

PCL-Coating Effects on Release Kinetics

PCL has been widely investigated as a matrix material for the fabrication of controlled release drug delivery systems. The biocompatibility of PCL has also been well established; PCL has been use in many polymer and drug formulations and has been useful for manipulating the rate of release of microspheres generated by other methods. The particles coated with PCL (i.e., PCL-coated bio-polymer-PEG) extended the release of their contents. PCL-coated bio-polymer-PEG particles gave particles in the size range of 5 nm to 50 µm. Particles were coated up to three times with PCL to increase the duration of the in vitro release kinetics of the encapsulation protein or drug. There was no marked difference in the size range between single, double and triple PCL-coated of the bio-polymer-PEG particles. Even though there was no difference in the particle size after coating, there was a significant difference in the rate of release of BSA among these systems. Single and double coatings of PCL resulted in 80% protein release in 5 and 30 days, respectively. Triple coating of particles with PCL correlated to 70 day in vitro release of 80% of their contents.

Host Cell Targeting by Peptide-Conjugated PCL-Coated Bio-Polymer-PEG Particles

Several studies have revealed peptides that specifically bind host cells. These peptides, once conjugated to the PCL used to coat the bio-polymer-PEG particles, allowed for cell-specific binding of PCL-coated bio-polymer-PEG particles containing vaccine antigen, cisplatin, gadolinium, and fluorescent or luminescent molecules. Selective binding of microparticles and binding plus uptake of nanoparticles by dendritic cells and B cells as well as prostate, breast, ovarian and lung cancer cells was achieved using these peptides.

Fluorescent Microscopy of Cancer Cells Treated with Cisplatin-Encapsulated Nanoparticle-Coated with Folic Acid Cancer cell lines were grown on chamber slides and incubated in culture medium containing nanoparticles comprised of cisplatin- plus TexasRed-encapsulated in starch with polycaprolactone-conjugated cancer-specific folic acid. Cells were washed in PBS three times to remove non-adherent nanoparticles and incubated for 1 hour. Subsequently cells were fixed and stained for tunnel positive cells. Results, on staining, indicated apoptosis.

Fluorescent Microscopy of Prostate Cancer Cells or Normal Prostatic Epithelial Cells Treated with Cisplatin-Encapsulated Nanoparticle Uncoated or Coated with Folic Acid or Targeting (In this Case, Tumor-Specific) Peptide Prostate cancer cells (PC3, DU145 and LNCaP) or prostatic epithelial cells (PrEC) were grown on chamber slides and incubated in culture medium containing nanoparticles containing cisplatin in starch and coated with polycaprolactone-conjugated cancer-specific folate or peptide or unconjugated negative controls. Cells were washed in PBS three times to remove non-adherent nanoparticles and incubated for 1 hour. Subsequently cells were fixed and stained for tunnel positive cells indicating apoptosis. The staining results showed positive evidence of apoptosis.

Localization of Bovine IgG after Oral Delivery Using Nanoparticles

Mice received a single oral dose of 100 μg of bovine IgG-encapsulated in polycaprolactone-coated nanoparticles in 200 μl PBS by gavage. Mice were sacrificed two days later. Intestine, liver, mesenteric lymph nodes (MLN) and kidneys were isolated, fixed in 10% formalin and paraffin-embedded. Subsequently, slides were stained with horse radish peroxidase (HRP)-conjugated rabbit anti-bovine IgG and developed by diaminobenzidine tetrahydrochloride (brown) and hematoxylin (blue) counter-staining staining. The staining pattern indicated the bovine IgG had been delivered to the tissues.

As indicated above, the nanoparticles can be administered orally. The active agents of the invention may be administered in the usual pharmaceutically-acceptable carriers, vehicles and/or adjuvants. The term parenteral as used herein includes, but is not limited to, subcutaneous, intravenous, and intramuscular administration. In the methods of the present invention, the compositions containing the biologically active agents may be administered, for example, parenterally, orally, by inhalation spray, rectally, nasally, buccally, vaginally, topically, or via an implanted reservoir in dosage formulations containing conventional non-toxic pharmaceutically acceptable carrier. The dosage and means of administration will depend on the action sought to be achieved by administration of the biologically active agent.

What is claimed is:

1. A pharmaceutical composition, comprising:

planetary ball milled nanoparticles comprising:

a biologically active agent;

polyethylene glycol; and at least one biopolymer selected from the group consisting of starch, cellulose, collagen, lactose and alginate, wherein the nanoparticles are coated with a coating agent comprising at least one of polycaprolactone and polyethylene glycol and wherein the planetary ball milled nanoparticles are prepared by a method comprising the steps of:

(a) mixing the at least one biopolymer dissolved in an aqueous solution with the biologically active agent to form a first mixture;

(b) mixing the first mixture with polyethylene glycol to form a second mixture;

(c) drying the second mixture;

(d) producing nanoparticles of the dried second mixture by planetary ball milling; and (e) coating the planetary ball milled nanoparticles with the coating agent.

2. The composition of claim 1, wherein said nanoparticles have a size range of 5-30 nm.

3. The composition of claim 1, wherein said nanoparticles have a size range of 30-180 nm.

4. The composition of claim 1, wherein the biologically active agent is an anti-cancer agent.

5. The composition of claim 4, wherein the anti-cancer agent is paclitaxel, or cisplatin.

6. The composition of claim 1, wherein the coating agent comprises polycaprolactone.

7. The composition of claim 6, wherein the coating agent further comprises a peptide conjugated to polycaprolactone.

8. The composition of claim 7, wherein the peptide binds specifically to a target cell.

9. The composition of claim 6, wherein the coating agent further comprises a folic acid conjugated to polycaprolactone.

10. The composition of claim 1, wherein the nanoparticles are coated with a single or double coating of polycaprolactone.

11. The composition of claim 1, wherein the nanoparticles are coated with a triple coating of polycaprolactone.

12. A pharmaceutical composition comprising:
planetary ball milled nanoparticles comprising:
an anti-cancer agent;
polyethylene glycol; and
at least one biopolymer selected from the group consisting of starch, cellulose, collagen, lactose and alginate,
wherein the nanoparticles have a size in the range of 5-30 nm, and wherein the particles are coated with a coating agent comprising polycaprolactone and wherein the planetary ball milled nanoparticles are prepared by a method comprising the steps of:
(a) mixing the at least one biopolymer dissolved in an aqueous solution with the anti-cancer agent to form a first mixture;
(b) mixing the first mixture with polyethylene glycol to form a second mixture;
(c) drying the second mixture;
(d) producing nanoparticles of the dried second mixture by planetary ball milling; and
(e) coating the planetary ball milled nanoparticles with the coating agent.

13. The pharmaceutical composition of claim 12, wherein the coating agent comprises polycaprolactone conjugated to a cancer-targeting peptide.

14. The pharmaceutical composition of claim 12, wherein the coating agent comprises polycaprolactone conjugated to a cancer-targeting antibody.

15. The pharmaceutical composition of claim 12, wherein the coating agent comprises polycaprolactone conjugated to folic acid.

16. A pharmaceutical composition, comprising:
planetary ball milled particles comprising:
an anti-cancer agent selected from the group of paclitaxel and cisplatin;
polyethylene glycol; and
a biopolymer selected from the group consisting of starch, cellulose, collagen, lactose and alginate,
wherein the particles have a size in the range of 5 nm to 50 µm, and wherein the particles are coated with one or more layers of polycaprolactone and wherein the planetary ball milled particles are prepared by a method comprising the steps of:
(a) mixing the biopolymer dissolved in an aqueous solution with the anti-cancer agent to form a first mixture;
(b) mixing the first mixture with polyethylene glycol to form a second mixture;
(c) drying the second mixture;
(d) producing particles of the dried second mixture by planetary ball milling; and
(e) coating the planetary ball milled particles with polycaprolactone.

17. The pharmaceutical composition of claim 16, wherein the particles are coated with one or two layers of polycaprolactone.

18. The pharmaceutical composition of claim 16, wherein the particles are coated with three layers of polycaprolactone.

19. The pharmaceutical composition of claim 16, wherein the polycaprolactone is conjugated to a cancer-targeting peptide.

20. The pharmaceutical composition of claim 16, wherein the polycaprolactone is conjugated to folic acid.

* * * * *